United States Patent [19]

Ondetti et al.

[11] 4,153,725
[45] May 8, 1979

[54] RELIEVING ANGIOTENSION RELATED HYPERTENSION WITH CARBOXYALKYLACYLAMINO ACIDS

[75] Inventors: Miguel A. Ondetti, Princeton; David W. Cushman, West Windsor, both of N.J.

[73] Assignee: E. R. Squibb & Sons, Inc., Princeton, N.J.

[21] Appl. No.: 903,290

[22] Filed: May 4, 1978

Related U.S. Application Data

[62] Division of Ser. No. 684,605, May 10, 1976, Pat. No. 4,105,789.

[51] Int. Cl.² ............... A61K 31/195; A61K 31/215; C07C 103/84
[52] U.S. Cl. ............................ 424/309; 424/273 R; 424/274; 424/313; 424/316; 424/318; 424/319
[58] Field of Search ............... 424/273 R, 274, 309, 424/313, 316, 318, 319

[56] References Cited

U.S. PATENT DOCUMENTS

| 3,462,535 | 8/1969 | Loew et al. | 560/41 |
| 3,551,419 | 12/1970 | Re et al. | 260/518 R |
| 3,852,338 | 12/1974 | Kaiser et al. | 424/309 |
| 3,896,166 | 7/1975 | Kaiser et al. | 424/309 |

OTHER PUBLICATIONS

Berse et al., J. Org. Chem., vol. 27, 1962, pp. 3489–3495.
Vasilevskii et al., Zh, Org. Khimii, vol. 2, 1970, pp. 244–249.

*Primary Examiner*—Anna P. Fagelson
*Attorney, Agent, or Firm*—Lawrence S. Levinson; Merle J. Smith

[57] ABSTRACT

New carboxyalkylacylamino acids which have the general formula

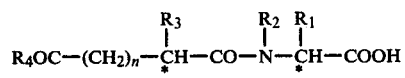

are useful as angiotensin converting enzyme inhibitors.

19 Claims, No Drawings

RELIEVING ANGIOTENSION RELATED HYPERTENSION WITH CARBOXYALKYLACYLAMINO ACIDS

This is a division, of application Ser. No. 684,605, filed May 10, 1976, now U.S. Pat. No. 4,105,789.

SUMMARY OF THE INVENTION

This invention relates to new carboxyalkylacylamino acids and related compounds which have the general formula

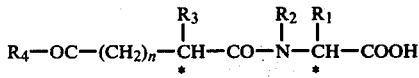

and salts thereof, wherein $R_1$ is hydrogen, lower alkyl, phenyl-lower alkylene, hydroxy-lower alkylene, hydroxyphenyl-lower alkylene, amino-lower alkylene, guanidino-lower alkylene, mercapto-lower alkylene, lower alkyl-mercapto-lower alkylene, imidazolyl-lower alkylene, indolyl-lower alkylene or carbamoyl-lower alkylene;

$R_2$ is hydrogen or lower alkyl;

$R_3$ is lower alkyl or phenyl lower alkylene;

$R_4$ is hydroxy, lower alkoxy or hydroxyamino; n is 1 or 2.

The asterisks indicate asymmetric carbon atoms.

DETAILED DESCRIPTION OF THE INVENTION

The invention in its broad aspects includes derivatives of amino acids and related compounds having formula I above. Within this broad group, because of their properties, certain subgroups are preferred over others.

Compounds in the group represented by formula I which are derived from or include the structure of the amino acids alanine, leucine, threonine, phenylalanine, lysine, arginine, glutamine, histidine, methionine, tyrosine, valine, asparagine or tryptophan are broadly preferred. Especially preferred modifications are compounds of formula I wherein n is 2, $R_1$ is guanidino-lower alkylene (particularly guanidinopropyl), amino-lower alkylene (particularly amino-$C_3$-$C_4$-lower alkylene) or phenyl-lower alkylene (particularly phenylmethyl); $R_2$ is hydrogen or lower alkyl (particularly hydrogen or methyl); $R_3$ is lower alkyl (particularly methyl); and $R_4$ is hydroxy or hydroxyamino.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The lower alkylene groups are of the same kind having 1 to 7 carbons. Similarly the lower alkoxy groups are of the same kind with a link to oxygen, for example, methoxy, ethoxy, propoxy, isopropoxy, butoxy, isobutoxy, t-butoxy and the like. The $C_1$-$C_4$ members, especially $C_1$ and $C_2$ members, of all types are preferred. Phenylmethyl is the preferred phenyl-lower alkylene group and methoxy the preferred lower alkoxy group.

The products of formula I and the preferred subgroups can be produced by various methods of synthesis. According to a preferred method, an acid of the formula

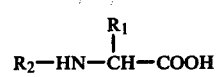

wherein $R_1$ and $R_2$ are defined as above is coupled with a monoester of a succinic or glutaric acid of the formula

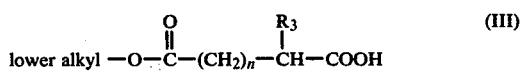

wherein $R_3$ has the meaning defined above, by one of the known procedures in which the acid III is activated, prior to reaction with the acid II, involving formation of a mixed anhydride, symmetrical anhydride, acid chloride, active ester, Woodward reagent K, N,N'-carbonylbisimidazole, active ester, Woodward reagent K, N,N'-carbonylbisimidazole, EEDQ (N-ethoxycarbonyl-2-ethoxy-1,2-dihydroquinoline) or the like. [For a review of these methods, see Methoden der Organischen Chemie (Houben-Weyl) Vol. XV, parts 1 and 2 (1974)].

The product of this reaction is a compound of the formula

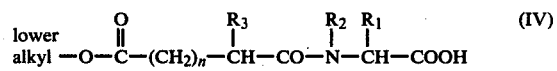

which is saponified, e.g., with a base like sodium hydroxide, in conventional manner to obtain the free di-acid

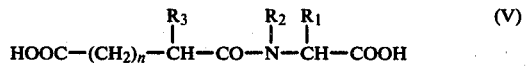

Conversely the free acid can be esterified by conventional procedures.

As a modification of the above procedure, an ester of the acid of formula II, e.g., a lower alkyl ester or an aralkyl ester, can be used in the reaction with the monoester of formula III to obtain a compound of the formula

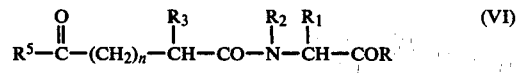

wherein R and $R^5$ are ester groups, e.g., lower alkoxy or aralkyloxy. Other coupling reagents such as dicyclohexylcarbodiimide can be used in addition to those referred to above.

Hydroxylaminolysis of the acid IV or treatment of the acid IV with hydroxylamine yields the hydroxamic acid

The succinic acid monoesters of formula III (i.e., n is 1) are prepared by alcoholysis of the corresponding substituted succinic anhydride. It is preferred to obtain products wherein the ester function is $\beta$ to the alkyl side chain.

In order to obtain the required regiospecificity in the alcoholysis reaction, an alkylidene succinic anhydride is preferably used to obtain the starting monoester, e.g., an anhydride of the formula

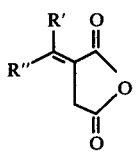
(VIII)

wherein R' is hydrogen, lower alkyl or phenyl and R" is hydrogen or lower alkyl.

This is treated with an alcohol R'''OH to obtain the product

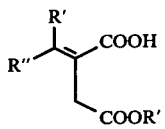
(IX)

then reduction with hydrogen yields the monoester

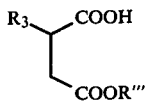
(X)

Similarly, in the case of the glutaric acids, (i.e., n is 2), alkylidene derivatives are used. When such alkylidene derivatives are not readily available, the substituted glutaric anhydride is subjected to alcoholysis followed by careful purification of the monoester by fractional crystallization of the dicyclohexylammonium salt.

Products of formula I have at least one asymmetric carbon and two if $R_1$ is other than hydrogen. These carbon atoms are indicated by an asterisk in formula I. The compounds accordingly exist in diastereoisomeric forms or in racemic mixtures thereof. All of these are within the scope of the invention. The above described synthesis can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the amino acid constitutes the preferred isomeric form.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product, as illustrated in the examples in the case of the dicyclohexylamine salt.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form [e.g., polystyrene sulfonic acid resin—Dowex 50 (Mikes, Laboratory Handbook of Chromatographic Methods (Van Nostrand, 1961) page 256] or with an aqueous acid and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance present which has been implicated as the causative agent in various forms of hypertension in various mammalian species, e.g., rats, dogs, etc. The compounds of this invention intervene in the renin→angiotensin I→angiotensin II sequence by inhibiting angiotensin converting enzyme and reducing or eliminating the formation of the pressor substance angiotensin II. Thus by the administration of a composition containing one or a combination of compounds of formula I or physiologically acceptable salt thereof, angiotensin dependent hypertension in the species of mammal suffering therefrom is alleviated. A single dose, or preferably two to four divided daily doses, provided on a basis of about 1 to 1000 mg. per kilogram per day, preferably about 10 to 100 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143 (1973). The substance is preferably administered orally, but parenteral routes such as subcutaneously, intramuscularly, intravenously or intraperitoneally can also be employed.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are illustrative of the invention and constitute especially preferred embodiments. All temperatures are in degrees celsius.

EXAMPLE 1

N-(3-Methoxycarbonyl-2-methylpropanoyl)-L-alanine benzyl ester

L-alanine benzyl ester (44.7 g.) and hydroxybenzotriazole (34 g.) are dissolved in dioxane (750 ml.) and the solution is chilled with stirring in an ice-water bath. Dicyclohexylcarbodiimide (51.5 g.) and 3-methoxycarbonyl-2-methylpropanoic acid (36 g.), prepared by hydrogenation of 3-methoxycarbonyl-2-methylene propanoic acid, are added in that order and the mixture is stirred at room temperature for 18 hours. The precipitate is filtered off, and the filtrate is concentrated to dryness in vacuo. The residue is dissolved in ethyl acetate and washed neutral. The ethyl acetate is dried over magnesium sulfate and concentrated to dryness in vacuo to yield N-(3-methoxycarbonyl-2-methylpropanoyl)-L-alanine benzyl ester.

EXAMPLE 2

N-(3-Methoxycarbonyl-2-methylpropanoyl)-L-alanine

N-(3-methoxycarbonyl-2-methylpropanoyl)-L-alanine benzyl ester (50 g.) is dissolved in 95% ethanol, 10% palladium on charcoal (5 g.) is added and the mixture is hydrogenated at normal pressure for 16 hours. The catalyst is filtered off and the filtrate is concentrated to dryness in vacuo to yield N-(3-methoxycarbonyl-2-methylpropanoyl)-L-alanine.

EXAMPLE 3

N-(3-Carboxy-2-methylpropanoyl)-L-alanine

N-(3-methoxycarbonyl-2-methylpropanoyl)-L-alanine (9.7 g.) is dissolved in a mixture of methanol (137 ml.) and N sodium hydroxide (137 ml.) and the solution is stirred at room temperature for five hours. The free diacid is isolated by chromatography on a Dowex 50 ion exchange resin.

EXAMPLE 4

N (3-hydroxycarbamoyl-2-methylpropanoyl)-L-alanine

N-(3-methoxycarbonyl-2-methylpropanoyl)-L-alanine (2.17 g.) is dissolved in absolute ethanol (8 ml.). An ethanolic solution of hydroxylamine [prepared from hydroxylamine hydrochloride (0.7 g.) and sodium ethylate] is added followed by a solution of sodium (0.23 g.) in absolute ethanol (8 ml.). After two hours, the reaction mixture is added to vigorously stirred ether (500 ml.). The precipitate is filtered and dried to obtain N-(3-hydroxycarbamoyl-2-methylpropanoyl)-L-alanine sodium salt. The free acid is prepared by treatment with an ion exchange resin (Dowex 50 in the hydrogen form).

EXAMPLE 5

N-(3-carboxy-2-methylpropanoyl)-L-leucine

By substituting L-leucine benzyl ester for the L-alanine benzyl ester in the procedure of Example 1, and then treating the product by the procedures of Examples 2 and 3, N-(3-methoxycarbonyl-2-methylpropanoyl)-L-leucine benzyl ester, N-(3-methoxycarbonyl-2-methylpropanoyl)-L-leucine, and N-(3-carboxy-2-methylpropanoyl)-L-leucine are obtained.

EXAMPLE 6

N-(3-hydroxycarbamoyl-3-methylpropanoyl)-L-leucine

By substituting N-(3-methoxycarbonyl-2-methylpropanoyl)-L-leucine for N-(3-methoxycarbonyl-2methylpropanoyl)-L-alanine in the procedure of Example 4, N-(3-hydroxycarbamoyl-2-methylpropanoyl)-L-leucine is obtained.

EXAMPLE 7

N-(3-Carboxy-2-methylpropanoyl)-L-threonine

By substituting O-benzyl-L-threonine benzyl ester for the L-alanine benzyl ester in the procedure of Example 1, and then treating the product by the procedures of Examples 2 and 3, N-(3-methoxycarbonyl-2-methylpropanoyl)-O-benzyl-L-threonine benzyl ester, N-(3-methoxycarbonyl-2-methyl-propanoyl)-L-threonine and N-(3-carboxy-2-methylpropanoyl)-L-threonine are obtained.

EXAMPLE 8

N-(3-hydroxycarbamoyl-2-methylpropanoyl)-L-threonine

By substituting N-(3-methoxycarbonyl-2-methylpropanoyl)-L-threonine for N-(3-methoxycarbonyl-2-methylpropanoyl)-L-alanine in the procedure of Example 4, N-(3-hydroxycarbamoyl-2-methylpropanoyl)-L-threonine is obtained.

EXAMPLE 9

N-(3-carboxy-2-methylpropanoyl)-L-phenylalanine

By substituting L-phenylalanine benzyl ester for the L-alanine benzyl ester in the procedure of Example 1, and then treating the product by the procedures of Examples 2 and 3, N-(3-methoxycarbonyl-2-methylpropanoyl)-L-phenylalanine benzyl ester, N-(3-methoxycarbonyl-2-methylpropanoyl)-L-phenylalanine and N-(3-carboxy-2-methylpropanoyl)-L-phenylalanine are obtained.

EXAMPLE 10

N-(3-hydroxycarbamoyl-2-methylpropanoyl)-L-phenylalanine

By substituting N-(3-methoxycarbonyl-2-methylpropanoyl)-L-phenylalanine for N-(3-methoxycarbonyl-2-methylpropanoyl)-L-alanine in the procedure of Example 4, N-(3-hydroxycarbamoyl-2-methylpropanoyl)-L-phenylalanine is obtained.

EXAMPLE 11

$N^\alpha$-(3-carboxy-2-methylpropanoyl)-L-lysine

By substituting $N^\epsilon$-benzyloxycarbonyl-L-lysine benzyl ester for the L-alanine benzyl ester in the procedure of Example 1, and then treating the product by the procedure of Examples 2 and 3, $N^\alpha$-(3-methoxycarbonyl-2-methylpropanoyl)-N$^\epsilon$-benzyloxycarbonyl-L-lysine benzyl ester, N$^\alpha$-(3-methoxycarbonyl-2-methylpropanoyl)-L-lysine, and N$^\alpha$-(3-carboxy-2-methylpropanoyl)-L-lysine are obtained.

EXAMPLE 12

N$^\alpha$-(3-hydroxycarbamoyl-2-methylpropanoyl)-L-lysine

By substituting N$^\alpha$-(3-methoxycarbonyl-2-methylpropanoyl)-L-lysine for N-(3-methoxycarbonyl-2-methylpropanoyl)-L-alanine in the procedure of Example 4, N$^\alpha$-(3-hydroxycarbamoyl-2-methylpropanoyl)-L-lysine is obtained.

EXAMPLE 13

N$^\alpha$-(3-carboxy-2-methylpropanoyl)-L-arginine

By substituting nitro-L-arginine benzyl ester for the L-alanine in the procedure of Example 1, and then treating the product by the procedures of Examples 2 and 3, N$^\alpha$-(3-methoxycarbonyl-2-methylpropanoyl)-nitro-L-arginine benzyl ester, N$^\alpha$-(3-methoxycarbonyl-2-methylpropanoyl)-L-arginine and N$^\alpha$-(3-carboxy-2-methylpropanoyl-L-arginine are obtained.

EXAMPLE 14

N$^\alpha$-(3-hydroxycarbamoyl-2-methylpropanoyl)-L-arginine

By substituting N$^\alpha$-(3-methoxycarbonyl-2-methylpropanoyl-L-arginine for the N-(3-methoxycarbonyl-2-methylpropanoyl)-L-alanine in the procedure of Example 4, N$^\alpha$-(3-hydroxycarbamoyl-2-methylpropanoyl)-L-arginine is obtained.

EXAMPLE 15

N-(3-carboxy-2-methylpropanoyl)-L-glutamine

By substituting L-glutamine benzyl ester for the alanine benzyl ester in the procedure of Example 1, and then treating the product by the procedure of Examples 2 and 3, N-(3-methoxycarbonyl-2-methylpropanoyl)-L-glutamine benzyl ester, N-(3-methoxycarbonyl-2-methylpropanoyl)-L-glutamine and N-(3-carboxy-2-methylpropanoyl)-L-glutamine are obtained.

EXAMPLE 16

N-(3-hydroxycarbamoyl-2-methylpropanoyl)-L-glutamine

By substituting N-(3-methoxycarbonyl-2-methylpropanoyl)-L-glutamine for the N-(3-methoxycarbonyl-2-methylpropanoyl)-L-alanine in the procedure of Example 4, N-(3-hydroxycarbamoyl-2-methylpropanoyl)-L-glutamine is obtained.

EXAMPLE 17

N-(3-carboxy-2-methylpropanoyl)-L-histidine

By substituting L-histidine p-nitrobenzyl ester for the L-alanine benzyl ester in the procedure of Example 1 and then treating the product by the procedures of Examples 2 and 3, N-(3-methoxycarbonyl-2-methylpropanoyl)-L-histidine p-nitrobenzyl ester, N-(3-methoxycarbonyl-2-methylpropanoyl)-L-histidine, and N-(3-carboxy-2-methylpropanoyl)-L-histidine are obtained.

EXAMPLE 18

N-(3-hydroxycarbamoyl-2-methylpropanoyl)-L-histidine

By substituting N-(3-methoxycarbonyl-2-methylpropanoyl)-L-histidine for the N-(3-methoxycarbonyl-2-methylpropanoyl)-L-alanine in the procedure of Example 4, N-(3-hydroxycarbamoyl-2-methylpropanoyl)-L-histidine is obtained.

EXAMPLE 19

N-(3-carboxy-2-methylpropanoyl)-L-methionine

By substituting L-methionine methyl ester for the L-alanine benzyl ester in the procedure of Example 1, and then treating the product by the procedure of Example 3, N-(3-methoxycarbonyl-2-methylpropanoyl)-L-methionine methyl ester, and N-(3-carboxy-2-methylpropanoyl)-L-methionine are obtained.

EXAMPLE 20

N-(3-carboxy-2-methylpropanoyl)-L-tyrosine

By substituting L-tyrosine benzyl ester for the L-alanine benzyl ester in the procedure of Example 1, and then treating the product by the procedure of Examples 2 and 3, N-(3-methoxycarbonyl-2-methylpropanoyl)-L-tyrosine benzyl ester, N-(3-methoxycarbonyl-2-methylpropanoyl)-L-tyrosine and N-(3-carboxy-2-methylpropanoyl)-L-tyrosine are obtained.

EXAMPLE 21

N-(3-methoxycarbonyl-2-benzylpropanoyl)-L-phenylalanine

3-Methoxycarbonyl-2-D-benzylpropanoic acid (4.4 g.) is dissolved in dioxane (40 ml.). N-hydroxysuccinimide (2.3 g.) and dicyclohexylcarbodiimide (4.12 g.) are added and the mixture is stirred at room temperature overnight. The precipitate is filtered and the filtrate is concentrated to dryness and the residue is crystallized from ethyl acetate to yield 3.67 g. of 3-methoxycarbonyl-2-D-benzylpropanoic acid N-hydroxysuccinimide ester, m.p. 111°–113°. This ester (4.8 g.) dissolved in pyridine (24 ml.) is added to a suspension of L-phenylalanine (4.95 g.) in a solution of sodium bicarbonate (3.75 g.) in water (24 ml.). After eight hours the reaction mixture is diluted with water and extracted with ethyl acetate. The aqueous phase is acidified and extracted with ethyl acetate. This ethyl acetate is concentrated to dryness and the product is crystallized from ether to yield 2.1 g. of N-(3-methoxycarbonyl-2-D-benzylpropanoyl)-L-phenylalanine, m.p. 100°–104°.

EXAMPLE 22

N-(3-Carboxy-2-D-benzylpropanoyl)-L-phenylalanine

N-(3-Methoxycarbonyl-2-D-benzylpropanoyl)-L-phenylalanine (1.18 g.) is dissolved in dichloromethane (32 ml.) and the solution is chilled to −10°. Molar boron tribromide solution in dichloromethane (16 ml.) is added and the reaction is allowed to proceed 1 hour at −10° and 18 hours at room temperature. Water and ethyl acetate are added and the organic phase is separated and concentrated to dryness. The residue is crystallized from ethyl acetate to yield 0.5 g. of N-(3-carboxy-2-D-benzylpropanoyl)-L-phenylalanine m.p. 144°–145°.

EXAMPLE 23

N-(4-Methoxycarbonyl-2-methylbutanoyl)-L-alanine benzyl ester (a) 4-methoxycarbonyl-2-methylbutanoic acid 2-Methylglutaric acid (14.6 g.) and acetyl chloride (26 ml.) are heated in the steam bath for one hour. The mixture is concentrated to dryness in vacuo and the residue is evaporated twice from toluene. The residue is dissolved in methanol (4.7 ml.) and heated on the steam bath for one hour and concentrated to dryness. The residue is dissolved in a mixture of ether (17 ml.), dicyclohexylamine (16.7 ml.) and hexane (83 ml.). The crystalline salt is filtered off and the filtrate is concentrated to one third volume and chilled. The crystals are filtered and dried to yield 11.3 g. of 4-methoxycarbonyl-2-methyl butanoic acid dicyclohexylamine salt, m.p. 97°–99°. The salt is converted to the free acid by distribution between ethyl acetate and aqueous acid.

(b) 4-methoxycarbonyl-2-methylbutanoic acid (3.1 g.), L-alanine benzyl ester (3.58 g.) and hydroxybenzotriazole (2.7 g.) are dissolved in dichloromethane. The solution is chilled in the ice bath and dicyclohexylcarbodiimide (4.12 g.) is added. After stirring 15 minutes in the ice bath and 18 hours at room temperature the precipitate is filtered off and the filtrate is concentrated to dryness. The residue is dissolved in ethyl acetate and washed neutral. The organic phase is dried over magnesium sulfate and concentrated to dryness to yield N-(4-methoxycarbonyl-2-methylbutanoyl)-L-alanine benzyl ester.

EXAMPLE 24

N-(4-Methoxycarbonyl-2-methylbutanoyl)-L-alanine

N-(4-methoxycarbonyl-2-methylbutanoyl-L-alanine benzyl ester (4 g.) is dissolved in 95% ethanol (40 ml.) 10% palladium on charcoal (0.5 g.) is added and the mixture is hydrogenated at normal pressure for 16 hours. The catalyst is filtered off and the filtrate is concentrated to dryness in vacuo to give N-(4-methoxycarbonyl-2-methylbutanoyl)-L-alanine.

EXAMPLE 25

N-(4-Hydroxycarbamoyl-2-methylbutanolyl)-L-alanine

By substituting N-(3-methoxycarbonyl-2-methylbutanoyl)-L-alanine for the N-(4-methoxycarbonyl-2-methylpropanoyl)-L-alanine in the procedure of Example 4, N-(4-hydroxycarbamoyl-2-methylbutanoyl)-L-alanine is obtained.

EXAMPLE 26

N-(4-Carboxy-2-methylbutanoyl)-L-alanine

N-(4-methoxycarbonyl-2-methylbutanoyl)-L-alanine (9.0 g.) is dissolved in a mixture of methanol (130 ml.) and N-sodium hydroxide (13 ml.) and the solution is stirred at room temperature for five hours. The free diacid is isolated by chromatography on a Dowex 50 ion exchange column.

EXAMPLE 27

N-(4-Carboxy-2-methylbutanoyl)-L-valine

By substituting L-valine benzyl ester for the L-alanine benzyl ester in the procedure of Example 23 and then treating the product by the procedure of Examples 24 and 26, N-(4-methoxycarbonyl-2-methylbutanoyl)-L-valine benzyl ester, N-(4-methoxycarbonyl-2-methylbutanoyl)-L-valine and N-(4-carboxy-2-methylbutanoyl)-L-valine are obtained.

EXAMPLE 28

N-(4-Hydroxycarbamoyl-2-methylbutanoyl)-L-valine

By substituting N-(4-methoxycarbonyl-2-methylbutanoyl)-L-valine for N-(3-methoxycarbonyl-2-methylpropanoyl)-L-alanine in the procedure of Example 4, N-(4-hydroxycarbamoyl-2-methylbutanoyl)-L-valine is obtained.

EXAMPLE 29

N-(4-Carboxy-2-methylbutanoyl)-L-threonine

By substituting O-benzyl-L-threonine benzyl ester for L-alanine benzyl ester in the procedure of Example 23, and then treating th product by the procedures of Examples 24 and 26, N-(4-methoxycarbonyl-2-methylbutanoyl)-L-benzyl-L-threonine benzyl ester, N-(4-methoxycarbonyl-2-methylbutanoyl)-L-threonine, and N-(4-carboxy-2-methylbutanoyl)-L-threonine are obtained.

EXAMPLE 30

N-(4-Hydroxycarbamoyl-2-methylbutanoyl)-L-threonine

By substituting N-(4-methoxycarbonyl-2-methylbutanoyl)-L-threonine for the (3-methoxycarbonyl-2-methylpropanoyl)-L-analine in the procedure of Example 4, N-(4-hydroxycarbamoyl-2-methylbutanoyl)-L-threonine is obtained.

EXAMPLE 31

N-(4-Carboxy-2-methylbutanoyl)-L-asparagine

By substituting L-asparagine p-nitrobenzyl ester for the L-alanine benzyl ester in the procedure of Example 23, and then treating the product by the procedures of Examples 24 and 26, N-(4-methoxycarbonyl-2-methylbutanoyl)-L-asparagine p-nitrobenzyl ester, N-(4-methoxycarbonyl-2-methylbutanoyl)-L-asparagine and N-(4-carboxy-2-methylbutanoyl)-L-asparagine are obtained.

EXAMPLE 32

N-(4-Hydroxycarbamoyl-2-methylbutanoyl)-L-asparagine

By substituting N-(4-methoxycarbonyl-2-methylbutanoyl)-L-asparagine for the N-(3-methoxycarbonyl-2-methylpropanoyl)-L-alanine in the procedure of Example 4, N-(4-hydroxycarbamoyl-2-methylpropanoyl)-L-asparagine is obtained.

EXAMPLE 33

$N^\alpha$-(4-carboxy-2-methylbutanoyl)-L-lysine

By substituting $N^\epsilon$-benzyloxycarbonyl-L-lysine benzyl ester for the L-alanine benzyl ester in the procedure of Example 23 and then treating the product by the procedure of Examples 24 and 26, $N^\alpha$-(4-methoxycarbonyl-2-methylbutanoyl)-$N^\epsilon$-benzyloxycarbonyl-L-lysine benzyl ester, $N^\alpha$-(4-methoxycarbonyl-2-methylbutanoyl)-L-lysine and $N^\alpha$-(4-carboxy-2-methylbutanoyl)-L-lysine are obtained.

EXAMPLE 34

Nα-(4-Hydroxycarbamoyl-2-methylbutanoyl)-L-lysine

By substituting Nα-(4-,methoxycarbonyl-2-methylbutanoyl)-L-lysine for the N-(3-methoxycarbonyl-2-methylpropanoyl)-L-alanine in the procedure of Example 4, Nα-(4-hydroxycarbamoyl-2-methylbutanoyl)-L-lysine is obtained.

EXAMPLE 35

Nα-(4-Carboxy-2-methylbutanoyl)-L-arginine

By substituting nitro-L-arginine benzyl ester for the L-alanine benzyl ester in the procedure of Example 23, and then treating the product by the procedures of Examples 24 and 26, Nα-(4-methoxycarbonyl-2-methylbutanoyl)-nitro-L-arginine benzyl ester, Nα-(4-methoxycarbonyl-2-methylbutanoyl)-L-arginine, and Nα-(4-carboxy-2-methylbutanoyl)-L-arginine are obtained.

EXAMPLE 36

Nα-(4-Hydroxycarbamoyl-2-methylbutanoyl)-L-arginine

By substituting Nα-(4-methoxycarbonyl-2-methylbutanoyl)-L-arginine for the N-(3-methoxycarbonyl-2-methylpropanoyl)-L-alanine in the procedure of Example 4, Nα-(4-hydroxycarbamoyl-2-,ethylbutanoyl)-L-arginine is obtained.

EXAMPLE 37

Nα(4-Carboxy-2-methylbutanoyl)-L-histidine

By substituting L-histidine p-nitrobenzyl ester for the L-alanine benzyl ester in the procedure of Example 23, and then treating the product by the procedures of Examples 24 and 26, Nα-(4-methoxycarbonyl-2-methylbutanoyl)-L-histidine p-nitrobenzyl ester, Nα-(4-methoxycarbonyl-2-methylbutanoyl)-L-histidine, and Nα-(4-carboxy-2methylbutanoyl)-L-histidine are obtained.

EXAMPLE 38

Nα-(4-Hydroxycarbamoyl-2-methylbutanoyl)-L-histidine

By substituting Nα-(4-methoxycarbonyl-2-methylbutanoyl)-L-histidine for the N-(3-methoxycarbonyl-2-methylpropanoyl)-L-alanine in the procedure of Example 4, Nα-(4-hydroxycarbamoyl-2-methylbutanoyl)-L-histidine is obtained.

EXAMPLE 39

N-(4-Carboxy-2-methylbutanoyl)-L-methionine

By substituting L-methionine methyl ester for the L-alanine benzyl ester in the procedure of Example 23, and then treating the product by the procedure of Example 26, N-(4-methoxycarbonyl-2-methylbutanoyl)-L-methionine methyl ester and N-(4-carboxy-2-methylbutanoyl)-L-methionine are obtained.

EXAMPLE 40

N-(4-Carboxy-2-methylbutanoyl)-L-tryptophane

By substituting L-tryptophane benzyl ester for the L-alanine benzyl ester in the procedure of Example 23, and then treating the product by the procedures of Examples 24 and 26, N-(4-methoxycarbonyl-2-methylbutanoyl)-L-tryptophane benzyl ester, N-(4-methoxycarbonyl-2-methylbutanoyl)-L-tryptophane and N-(4-carboxy-2-methylbutanoyl)-L-tryptophane are obtained.

EXAMPLE 41

N-(4-Carboxy-2-methylbutanoyl)-L-tyrosine

By substituting L-tyrosine benzyl ester for the L-alanine benzyl ester in the procedure of Example 23, and then treating the product by the procedure of Examples 24 and 26, N-(4-methoxycarbonyl-2-methylbutanoyl)-L-tyrosine benzyl ester, N-(4-methoxycarbonyl-2-methylbutanoyl)-L-tyrosine, and N-(4-carboxy-2-,ethylbutanoyl)-L-tyrosine are obtained.

EXAMPLE 42

N-(4-Hydroxycarbamoyl-2-methylbutanoyl)-L-tyrosine

By substituting N-(4-methoxycarbonyl-2-methylbutanoyl)-L-tyrosine for the N-(3-methoxycarbonyl-2-methylpropanoyl)-L-alanine in the procedure of Example 4, N-(4-hydroxycarbamoyl-2-methylpropanoyl)-L-tyrosine is obtained.

The racemic forms of the final products in each of the foregoing examples are produced by utilizing the DL-form of the starting amino acid instead of the L-form.

Similarly the D-form of the final products in each of the foregoing examples is produced by utilizing the D-form of the starting amino acid instead of the L-form.

EXAMPLE 43

1000 tablets each containing 100 mg. of Nα-(3-carboxy-2-methylpropanoyl)-L-arginine are produced from the following ingredients:

| | |
|---|---|
| Nα-(3-carboxy-2-methylpropanoyl)-l-arginine | 100 g. |
| Corn starch | 50 g. |
| Gelatin | 7.5 g. |
| Avicel (microcrystalline cellulose) | 25 g. |
| Magnesium stearate | 2.5 g. |

The Nα-(3-carboxy-2-methylpropanoyl)-L-arginine and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 100 g. of active ingredient.

EXAMPLE 44

Two piece #1 gelatin capsules each containing 250 mg. of Nα-(3-hydroxycarbamoyl-2-methylpropanoyl)-L-lysine are filled with a mixture of the following ingredients:

| | |
|---|---|
| Nα-(3-hydroxycarbamoyl-2-methylpropanoyl)-L-lysine | 250 mg. |
| Magnesium stearate | 7 mg. |
| USP Lactose | 193 mg. |

What is claimed is:

1. A method for relieving angiotensin related hypertension in mammalian species suffering therefrom which comprises administering a composition containing an effective amount of a compound of the formula

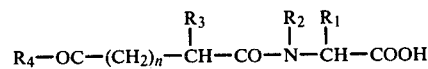

and salts thereof, wherein
  $R_1$ is hydrogen, lower alkyl, phenyl-lower alkylene, hydroxy-lower alkylene, hydroxyphenyl-lower alkylene, amino-lower alkylene, guanidino-lower alkylene, or carbamoyl-lower alkylene;
  $R_2$ is hydrogen or lower alkyl;
  $R_3$ is phenyl-lower alkylene;
  $R_4$ is hydroxy or lower alkoxy; and n is 1 or 2.

2. A method as in claim 1 wherein in the formula $R_4$ is hydroxy.

3. A method as in claim 1 wherein in the formula n is 2.

4. A method as in claim 1 wherein in the formula $R_1$ is (4-hydroxyphenyl)methyl.

5. A method as in claim 1 wherein in the formula $R_1$ and $R_3$ each is phenylmethyl; $R_2$ is hydrogen; $R_4$ is hydroxy and n is 1.

6. A method as in claim 1 wherein in the formula $R_1$ is phenylmethyl; $R_2$ is hydrogen; $R_3$ is phenyl methyl; $R_4$ is hydroxy and n is 1.

7. A method as in claim 1 wherein in the formula $R_1$ is guanidino-lower alkylene, amino-lower alkylene or phenyl-lower alkylene; $R_2$ is hydrogen or lower alkyl; $R_3$ is phenyl-lower alkylene; and $R_4$ is hydroxy.

8. A method as in claim 7 wherein in the formula n is 2.

9. A method as in claim 1 wherein in the formula n is 1.

10. A method as in claim 9 wherein in the formula $R_1$ is guanidinopropyl, amino-$C_3$-$C_4$-lower alkylene or phenylmethyl; $R_2$ is hydrogen or methyl; $R_3$ is phenyl methyl; and $R_4$ is hydroxy.

11. A method as in claim 9 wherein in the formula $R_1$ is phenylmethyl; $R_2$ is hydrogen or methyl; $R_3$ is phenyl methyl; and $R_4$ is hydroxy.

12. A method as in claim 11 wherein in the formula $R_2$ is hydrogen and $R_4$ is hydroxy.

13. A method as in claim 11 wherein in the formula $R_2$ is hydrogen.

14. A method as in claim 9 wherein in the formula $R_1$ is aminobutyl; $R_2$ is hydrogen or methyl; $R_3$ is phenyl methyl and $R_4$ is hydroxy.

15. A method as in claim 14 wherein in the formula $R_2$ is hydrogen and $R_4$ is hydroxy.

16. A method as in claim 14 wherein in the formula $R_2$ is hydrogen.

17. A method as in claim 9 wherein in the formula $R_1$ is guanidinopropyl; $R_2$ is hydrogen or methyl; $R_3$ is phenyl methyl and $R_4$ is hydroxy or hydroxyamino.

18. A method as in claim 17 wherein in the formula $R_2$ is hydrogen and $R_4$ is hydroxy.

19. A method as in claim 17 wherein in the formula $R_2$ is hydrogen.

* * * * *

UNITED STATES PATENT AND TRADEMARK OFFICE
CERTIFICATE OF CORRECTION

PATENT NO. : 4,153,725
DATED      : May 8, 1979
INVENTOR(S): Miguel Angel Ondetti, David W. Cushman It is certified that error appears in the above-identified patent and that said Letters Patent are hereby corrected as shown below:

```
Column 10, line 18 "th" should read -- the --.
Column 11, line 27 delete ",ethylbutanoyl" and add
--- methylbutanoyl ---.
Column 12, line 12 delete ",ethylbutanoyl" and add
--- methylbutanoyl ---.
Column 12, line 34 delete "1" and add --- L ---.
Column 14, line 23 delete " or hydroxyamino".
```

Signed and Sealed this

Eleventh Day of September 1979

[SEAL]

Attest:

LUTRELLE F. PARKER
*Attesting Officer*    *Acting Commissioner of Patents and Trademarks*